United States Patent [19]
Ueda et al.

[11] Patent Number: 5,300,297
[45] Date of Patent: * Apr. 5, 1994

[54] FEED ADDITIVE FOR RUMINANTS

[75] Inventors: Satoshi Ueda; Takashi Iizuka; Haruo Heima; Makoto Ozawa; Takeshi Nagai; Hiroyuki Sato, all of Kawasaki, Japan

[73] Assignee: Ajinomoto Co., Inc., Tokyo, Japan

[*] Notice: The portion of the term of this patent subsequent to Jul. 13, 2010 has been disclaimed.

[21] Appl. No.: 45,099

[22] Filed: Apr. 12, 1993

Related U.S. Application Data

[63] Continuation-in-part of Ser. No. 820,379, Jan. 14, 1992, Pat. No. 5,227,166.

[30] Foreign Application Priority Data

Jan. 14, 1991 [JP] Japan ................................. 3-070265
Dec. 18, 1991 [JP] Japan ................................. 3-335073

[51] Int. Cl.⁵ .............................................. A23K 1/18
[52] U.S. Cl. ..................................... 424/438; 426/74; 426/807
[58] Field of Search ................... 424/438; 426/807, 74

[56] References Cited

U.S. PATENT DOCUMENTS 4,937,083  6/1990  Itagaki ................................. 426/69
4,976,976 12/1990  Itagaki ................................. 426/69
4,996,067  2/1991  Kobayashi ........................... 426/96
5,227,166  7/1993  Ueda ................................... 424/438
5,244,669  9/1993  Satoh ................................... 424/438

Primary Examiner—Gabrielle Phelan
Attorney, Agent, or Firm—Oblon, Spivak, McClelland, Maier & Neustadt

[57] ABSTRACT

The present invention relates to a biologically active substance that is stable in the rumen of ruminants and released in the abomasum and its subsequent digestive tract. The biologically active substance has the additional properties of being digested and absorbed with good efficiency.

8 Claims, No Drawings

FEED ADDITIVE FOR RUMINANTS

This is a continuation in part of application Ser. No. 820,379, filed Jan. 14, 1992, now U.S. Pat. No. 5,227,166.

BACKGROUND OF THE INVENTION

1. Field of the Invention

The present invention relates to feed additives for ruminants. More specifically, the present invention relates to a feed additive composition comprising a biologically active substance that is coated with a coating composition which is stable in the rumen of the ruminant and released in the abomasum or subsequent digestive tract. This ability makes it possible for the biologically active substance to be digested in the abomasum and subsequent digestive tract.

2. Description of the Background Art

In ruminant animals, such as cattle or sheep, the direct oral administration of biologically active substances, such as amino acids and vitamins, causes most of the substances to be decomposed by microorganisms in the rumen; thus they are not effectively utilized.

Accordingly, it is important to pass the biologically active substances through the rumen without decomposition by microorganisms to allow the biologically active substances to be effectively digested and absorbed in the abomasum and subsequent digestive tract. Such an ability would make an impact in the fields of feeds, nutrient preparations and veterinary drugs for ruminant animals.

It was proposed in the past to coat ruminant animal feed additives containing biologically active substances with protective substances, such as fatty acids, hardened animal oils and hardened vegetable oils. However, particles coated with these fats and oils are stable, not only in the rumen, but also in the abomasum and subsequent digestive tract making the biologically active substances difficult to be released in the abomasum and subsequent digestive tract.

For this reason, methods were proposed that added substances propelling the release of the biologically active substances in the abomasum and its subsequent digestive tract that contained such protective substances. In these methods, the biologically active substances are granulated and dispersed in coating materials or coated with coating materials.

The Japanese Laid-Open Patent Publication No. 168351/85 proposes a method of dispersing a biologically active substance in a protective substance which comprises granulating a biologically active substance containing at least 20% by weight of calcium carbonate and at least 10% by weight of a substance selected from the group consisting of monocarboxylic acid, a hardened oil and fat. Furthermore, Japanese Laid-Open Patent Publication No. 195653/86 proposes a process for dispersing a biologically active substance in coating materials composed of at least 10% by weight of a substance selected from the group consisting of a monocarboxylic acid, a hardened oil and fat, and at least 20% by weight to not more than 50% by weight of an insoluble salt of an acid which is more weakly acidic than hydrochloric acid.

As the method of coating with coating materials, for example, Japanese Laid-Open Patent Publication No. 317053/88 describes a method which comprises coating a biologically active substance with a coating material containing the protective substance composed of a monocarboxylic acid, hardened oil, lecithin, and a glycerin fatty acid ester.

However, the method of dispersing a biologically active substance in a coating materials requires that the content of the biologically active substance be considerably decreased in order to retain the protectiveness because the substance is present near the surface of the particle. In view of the fact that the time of passing from rumen to abomasum is between 10 hours to several days, it is difficult to keep the biologically active substances that are present near the surface stable as it passes through the rumen. Furthermore, when the substance is coated with a coating material composed of lecithin, a glycerin fatty acid ester and an oil or a fat, the coated layer has insufficient strength and its protectiveness is diminished. In addition, lecithin and a glycerin fatty acid ester are expected to have an emulsification action of the oil and fat in the small intestine, but because of the length of time required to pass through the small intestine, the property to release the biologically active substances is still not sufficient.

Another method proposed utilizes the difference in pH between the rumen and the abomasum by coating with a polymer which is insoluble in the environment of the rumen but is soluble in the strongly acidic abomasum. Since an organic solvent used for both the coating and the coating agent becomes expensive, this procedure is not a fully satisfactory means.

In view of the foregoing problems, the need exists to provide a method that protects a biologically active substance stably in the rumen of a ruminant animal and yet allows efficient digestion and absorption in the abomasum and subsequent digestive tract.

The present invention provides for such a biologically active substance that can effectively be digested and absorbed by ruminant animals and be safe and economical. Thus, the above objectives have been achieved.

SUMMARY OF THE INVENTION

The present invention provides in one embodiment, a feed additive for ruminants comprising a core containing a biologically active substance and coating composition placed on the surface of the core.

The coating composition comprises lecithin, at least one inorganic substance which is stable under neutral conditions and soluble under acidic conditions, and at least one substance selected from the group consisting of straight-chain or branched-chain saturated or unsaturated monocarboxylic acids having 14 to 22 carbon atoms, salts thereof, hardened vegetable oils, hardened animal oils, and waxes.

In another embodiment, the present invention relates to a feed additive as describe above, wherein the lecithin is used in an amount of from 0.1% to 20% by weight and the inorganic substance is used in an amount from 0.1 to 10% by weight, based on the weight of the coating composition.

In yet another embodiment, the present invention relates to the feed additive described above wherein the inorganic substance is carbonate or a calcium salt of pyrophosphoric acid.

A further embodiment relates to a feed for ruminants that comprises the feed additive described above.

Various other objects and advantages of the present invention will become apparent from the following detailed description of the invention.

DETAILED DESCRIPTION OF THE INVENTION

The present invention relates to a feed additive comprising a core containing a biologically active substance which is coated with coating materials containing lecithin, inorganic substances which are stable under neutral conditions but soluble under acidic conditions, and at least one substance selected from the group consisting of straight-chain or branched-chain saturated or unsaturated monocarboxylic acids having 14 to 22 carbon atoms or salts thereof, hardened vegetable oils, hardened animal oils, and waxes. Such a feed additive dually provides excellent stability in the rumen and excellent dissolution in the abomasum and its subsequent digestive tract.

The feed additive for ruminants of this invention contain lecithin and inorganic substances in the coating materials which are stable under neutral conditions but soluble under acidic conditions. By utilizing the fact that the inside of the abomasum is acidic, the action of the inorganic substances and the emulsification action of fatty acids and hardened oils by lecithin in the small intestine leads to the property of releasing the biologically active substances in the abomasum and its subsequent digestive tract and the synergistic effect makes the dissolving property good. Furthermore, the addition of the inorganic acid salts increases the strength of the coating layer.

In the present invention, the biologically active substances are selected from at least one material from the group consisting of known nutrients, feeds containing them, drugs, such as amino acids and derivatives thereof, hydroxy homologous compounds of amino acids, proteins, hydrocarbons, vitamins and veterinary medicines.

Specifically, they include amino acids such as lysine, methionine, tryptophan and threonine, amino acid derivatives such as N-acylamino acid and N-hydroxymethylmethionine calcium salt, and lysine hydrochloride, hydroxy homologous compounds of amino acids such as 2-hydroxy-4-methylmercaptobutyric acid and salts thereof, powders of natural nutrients such as grain powders, feathers and fish powder, proteins such as casein, corn proteins and potato proteins, carbohydrates such as starch, cane sugar and glucose, vitamins and substances having a similar function such as vitamin A, vitamin A acetate, vitamin A palmitate, vitamins B, thiamine, thiamine hydrochloride, riboflavin, nicotinic acid, nicotinic acid amide, calcium pantothenate, choline pantothenate, pyridoxine hydrochloride, choline chloride, cyanocobalamine, biotin, folic acid, p-aminobenzoic acid, vitamin $D_2$, vitamin $D_3$ and vitamin E, antibiotics such as tetracyclic antibiotics, amino glycoside antibiotics, macrolide-type antibiotics, polyether-type antibiotics, insecticides such as negfon; vermicides such as piperazine, and hormones such as estrogen, stibestrol, hexestrol, tyroprotein and goitrogen.

There is no particular restriction in the preparative method of a core containing a biologically active substance. As required, a binder or a filler may be added and granules, preferably particles close to spherical in shape, are prepared by a known granulating method such as extrusion granulation, fluidized granulation, or stirring granulation.

Examples of the binder are cellulose derivatives such as hydroxypropylcellulose, methyl cellulose, or sodium carboxymethylcellulose, vinyl derivatives such as polyvinyl alcohol or polyvinylpyrrolidone, gum arabic, guaiac gum and sodium polyacrylate. Starch, proteins and crystalline cellulose may be used as the filler. If required, a specific gravity adjusting agent may be added such as calcium carbonate, calcium phosphonate and talc.

The coating materials for coating a core containing the biologically active substance comprises lecithin, at least one inorganic substance which is stable under neutral conditions, but soluble under acidic conditions and at least one substance selected from the group consisting of straight-chain or branched-chain saturated or unsaturated monocarboxylic acids having 14 to 22 carbon atoms, or salts thereof, hardened vegetable oils, hardened animal oils, and waxes.

Examples of monocarboxylic acids include myristic acid, palmitic acid, stearic acid, oleic acid, linoleic acid, and behenic acid. Salts of these may also be used. Examples of hardened vegetable oils include hardened palm oil, hardened soybean oil, hardened rapeseed oil, and hardened castor oil. Examples of hardened animal oils are hardened beef tallow and hog fat. Examples of waxes are carnauba wax and beeswax, natural waxes, synthetic waxes, and paraffin waxes.

Lecithin used in the invention is not required to be pure. Preferably, it may be prepared from soybean and egg yolk as materials.

Examples of the inorganic substance which are stable under neutral conditions and soluble under acidic conditions include magnesium carbonate, calcium carbonate, calcium phosphate, calcium pyrophosphate and mixtures thereof. Carbonates such as magnesium carbonate, calcium carbonate, and the calcium salt of pyrophosphoric acid are more preferred.

Other important inorganic substances within the invention are calcium hydrogen phosphate hydrates, $CaHPO_4 \cdot X\ H_2O$, such as calcium hydrogen phosphate dihydrate, $CaHPO_4 \cdot 2\ H_2O$; calcium dihydrogen pyrophosphate, $CaH_2P_2O_7$; magnesium pyrophosphate, $Mg_2P_2O_7$; magnesium hydrogen phosphate hydrates, $MgHPO_4 \cdot X\ H_2O$; aluminum phosphate, $AlPO_4$; magnesium hydroxide, $Mg(OH)_2$; aluminum hydroxide, $Al(OH)_3$; ferrous oxide, $FeO$; manganese oxide, $MnO$; zinc oxide, $ZnO$; sodium hydrogen carbonate, $NaHCO_3$; and ferric oxide, $Fe_2O_3$.

The coating composition of this invention is such that in all coating materials, it comprises 0.1 to 20% by weight of lecithin, 0.1 to 10% by weight of the inorganic substance which is stable under neutral conditions and soluble under acidic conditions, preferably 1 to 10% of lecithin and 1 to 10% of the inorganic substance. If the amount of lecithin in the coating materials exceeds 20% by weight, the strength of the coating layer is decreased and the protectiveness in the rumen is reduced. If the amount of lecithin is less than 0.1% by weight, the emulsification action is insufficient, and the dissolving action in the abomasum and its subsequent digestive tract decreases. If the amount of the inorganic substance which is stable at neutrality and soluble under acidic conditions exceeds 10% by weight, the protectiveness in the rumen decreases. If it is below 0.1% by weight, the action of the inorganic substance inside of the abomasum is insufficient.

The ruminant animal feed additive composition of this invention is characterized by the fact that the core containing the biologically active substance is coated with the coating composition.

The amount of the coating materials used to coat core substances is not restricted in any particular manner. It should be as little as possible because the amount of the biologically active substance is large. But it should be the amount in which the coating material can fully protect the biologically active substance in the rumen. Usually, it is coated in an amount of 10 to 300 parts by weight, preferably 15 to 150 parts by weight, per 100 parts by weight of the cores containing the biologically active substance.

There is no particular restriction on the method of coating either. It can be coated by an ordinary method such as a method of fluidized-bed coating, pan coating or melt coating.

The present invention will be illustrated by the following examples and comparative examples without being deemed limitative thereof.

EXAMPLES

The methods below were used in the following examples to evaluate the utility of the ruminant animal feed additive.

Stability in the rumen

About 2 g of the prepared sample was put in a 200 ml Erlenmeyer flask. 100 ml of the Mc Dougall buffer solution corresponding to the rumen juice was put in the container, and shaken for 48 hours at a temperature of 39° C. After shaking, the amount of the biologically active substance dissolved was analyzed, and the stability in the rumen was calculated.

The amount of amino acids dissolved in the biologically active substances in the examples were analyzed by liquid chromatography.

Mc Dougall buffer solution

The following reagents were dissolved in 1000 ml of water.

Sodium hydrogen carbonate: 7.43 g
Disodium phosphate 12-hydrate: 7.00 9
Sodium chloride: 0.34 g
Potassium chloride: 0.43 g
Magnesium chloride hexahydrate: 0.10 g
Calcium chloride: 0.05 g Dissolving Property in the abomasum After the stability test, the shaken sample was recovered and washed, and further put into a 200 ml Erlenmeyer flask. 40 ml of a Clark-Lubs buffer solution corresponding to the abomasum juice was added and shaken for 3 hours at 39° C.

After shaking, the amount of the biologically active substance dissolved was analyzed and the dissolving property in the abomasum was calculated.

Clark-Lubs buffer solution

A buffer solution obtained by dissolving the following reagents in 1000 ml of water. Potassium chloride: 3.73 g Hydrochloric acid: 2.1 ml.

Dissolving Property in the small intestines

After the dissolving property inside the abomasum was tested, the shaken sample was recovered, and further put into a 200 ml Erlenmeyer flask. 100 ml buffer solution corresponding to a small intestine juice was added and shaken for 24 hours at 39° C. After shaking, the amount of the biologically active substance dissolved was analyzed, and the dissolving property in the small intestines was calculated.

EXAMPLE 1

A kneader was charged with 325 g of L-lysine hydrochloride, 172.5 g of talc, 2.5 g of sodium carboxymethylcellulose and 135 g of water. They were kneaded and then by using an extruder having a screen with an opening size of 1.5 mm, a cylindrical granule was obtained. The granule obtained was molded by using a spherical granule producing machine (Marumerizer, Fuji Paudal Co., Ltd.) to obtain a granule similar to a spherical shape. The resulting spherical granule was dried by fluidized-bed dryer to obtain a core containing L-lysine hydrochloride.

The coating material prepared, which is 5 parts by weight of lecithin (soybean lecithin, manufactured by WAKO Pure Chemical Industries, Ltd.-food additive-was used) and 5 parts by weight of magnesium carbonate, was dispersed per 90 parts by weight of melted hardened beef tallow. The coating material was used in an amount of 67 parts by weight per 100 parts of the cores (the rate of coating 40%). The fluidized-bed coater (New Marumeizer, Fuji Paudal Co., Ltd.) was used.

The coated particles were subjected to the above evaluation tests and the results were as follows:

The dissolving rate in the rumen was 9%, the dissolving rate in the abomasum was 39%, and the dissolving rate in the small intestines was 40%.

EXAMPLE 2

The preparation was conducted in the same manner as in Example 1 except that in Example 2 calcium carbonate was used instead of magnesium carbonate.

The coated particles were subjected to the above evaluation tests and the results were as follows:

The dissolving rate in the rumen was 4%, the dissolving rate in the abomasum was 46%, and the dissolving rate in the small intestines was 36%.

EXAMPLE 3

The preparation was conducted in the same manner as in Example 2 except that in Example 3, the coating material was used in an amount of 43 parts by weight per 100 parts of the cores (the rate of coating 30%).

The coated particles were subjected to the above evaluation tests and the results were as follows:

The dissolving rate in the rumen was 12%, rate in the abomasum was 20%, and the dissolving rate in the small intestines was 58%.

EXAMPLE 4

The preparation was conducted in the same manner as in Example 2 except that in Example 4, the coating materials contain 10 parts by weight of lecithin and 5 parts by weight of calcium carbonate and was used in an amount of 33 parts by weight (the rate of coating 25%).

The coated particles were subjected to the above evaluation tests and the results were as follows:

The dissolving rate in the rumen was 19%, the dissolving rate in the abomasum was 46%, and the dissolving rate in the small intestines was 32%.

EXAMPLE 5

The preparation was conducted in the same manner as in Example 2 except that in Example 5, the coating materials contain 2 parts by weight of lecithin and 10 parts by weight of calcium carbonate and was used in an amount of 25 parts by weight (the rate of coating 20%).

The coated particles were subjected to the above evaluation tests, and the results were as follows:

The dissolving rate in the rumen was 14%, the dissolving rate in the abomasum was 31%, and the dissolving rate in the small intestines was 35%.

EXAMPLE 6

The preparation was conducted in the same manner as in Example 3 except that in Example 6, calcium pyrophosphate was used instead of calcium carbonate.

The coated particles were subjected to the above evaluation tests and the results were as follows:

The dissolving rate in the rumen was 7%, the dissolving rate in the abomasum was 49%, and the dissolving rate in the small intestines was 32%.

EXAMPLE 7

A kneader was charged with 375 g of D,L-methionine, 120 g of talc, 5 g of sodium carboxymethylcellulose and 150 g of water, and they were kneaded. The mixture was processed by using an extruder having a screen with an opening size of 1.5 m.m to obtain a cylindrical granule. The resulting granule was formed by a spherical shaping apparatus (Marumerizer, Fuji Paudal Co., Ltd.) to make a granule similar to a spherical shape. The spherical granule was dried by fluidized-bed dryer to obtain a core containing D,L-methionine.

The coating material prepared, which is 5 parts by weight of lecithin and 5 parts by weight of magnesium carbonate, was dispersed per 90 parts by weight of melted hardened beef tallow. The coating material was used in an amount of 43 parts by weight per 100 parts by weight of the core (the rate of coating 30%). The fluidized-bed coater (New Marumerizer) was used.

The coated particles were subjected to the above evaluation test and the results were as follows:

The dissolving rate in the rumen was 17%, the dissolving rate in the abomasum was 20%, and the dissolving rate in the small intestines was 60%.

EXAMPLE 8

The preparation was conducted in the same manner as in Example 7 except that in Example 8, calcium carbonate was used instead of magnesium carbonate.

The coated particles were subjected to the above evaluation tests and the results were as follows:

The dissolving rate in the rumen was 15%, the dissolving rate in the abomasum was 26%, and the dissolving rate in the small intestines was 59%.

EXAMPLE 9

The preparation was conducted in the same manner as in Example 8 except that in Example 9, the coating materials contain 10 parts by weight of lecithin and 2 parts by weight of calcium carbonate and was used in an amount of 33 parts by weight (the rate of coating 25%).

The coated particles were subjected to the above evaluation tests and the results were as follows:

The dissolving rate in the rumen was 21%, the dissolving rate in the abomasum was 38%, and the dissolving rate in the small intestines was 37%.

COMPARATIVE EXAMPLE 1

The preparation was conducted in the same manner as in Example 1 except that in this Example, the coating materials contain 10 parts by weight of calcium carbonate.

The coated particles were subjected to the above evaluation tests, and the results were as follows:

The dissolving rate in the rumen was 5%, the dissolving rate in the abomasum was 15%, and the dissolving rate in the small intestines was 16%.

COMPARATIVE EXAMPLE 2

The preparation was conducted in the same manner as in Example 3 except that in this Example, the coating materials contain 30 parts by weight of lecithin.

The coated particles were subjected to the above evaluation tests and the results were as follows:

The dissolving rate in the rumen was 71%, the dissolving rate in the abomasum was 27%, and the dissolving rate in the small intestines was 1%.

COMPARATIVE EXAMPLE 3

The preparation was conducted in the same manner as in Example 8 except that in this Example, the coating materials contain 30 parts by weight of calcium carbonate.

The coated particles were subjected to the above evaluation tests, and the results were as follows:

The dissolving rate in the rumen was 82%, the dissolving rate in the abomasum was 10%, and the dissolving rate in the small intestines was 3%.

The superior properties of feed additives of the present invention disclosed in examples 1 through 14 that are compared to the comparative examples of the prior art are summarized below in Tables 1-3.

TABLE 1

|  | Example | | | | | |
|---|---|---|---|---|---|---|
|  | 1 | 2 | 3 | 4 | 5 | 6 |
| Biologically active substance | L-lysine hydrochloride | L-lysine hydrochloride | L-lysine hydrochloride | L-lysine hydrochloride | L-lysine hydrochloride | L-lysine hydrochloride |
| Cores (parts by weight) | 100 | 100 | 100 | 100 | 100 | 100 |
| Coated layer (parts by weight) | 67 | 67 | 43 | 33 | 25 | 43 |
| Composition of the coating layer (%) | | | | | | |
| Beef tallow | 90 | 90 | 90 | 85 | 88 | 90 |
| Lecithin | 5 | 5 | 5 | 10 | 2 | 5 |
| Magnesium carbonate | 5 | — | — | — | — | — |
| Calcium carbonate | — | 5 | 5 | 5 | 10 | — |
| Calcium pyrophosphate | — | — | — | — | — | 5 |
| Dissolving | | | | | | |

TABLE 1-continued

|  | Example | | | | | |
| --- | --- | --- | --- | --- | --- | --- |
|  | 1 | 2 | 3 | 4 | 5 | 6 |
| rate (%) | | | | | | |
| Corresponding to the rumen | 9 | 4 | 12 | 19 | 14 | 7 |
| Corresponding to the abomasum | 39 | 46 | 20 | 46 | 31 | 49 |
| Corresponding to the small intestines | 40 | 36 | 58 | 32 | 35 | 32 |

TABLE 2

|  | Example | | | Comparative Example | | |
| --- | --- | --- | --- | --- | --- | --- |
|  | 7 | 8 | 9 | 1 | 2 | 3 |
| Biologically active substance | D,L-Methionine | D,L-Methionine | D,L-Methionine | Lysine hydrochloride | Lysine hydrochloride | D,L-Methionine |
| Cores (parts by weight) | 100 | 100 | 100 | 100 | 100 | 100 |
| Coated layer (parts by weight) | 43 | 43 | 33 | 67 | 43 | 43 |
| Composition of the coating layer (%) | | | | | | |
| Beef tallow | 90 | 90 | 88 | 90 | 70 | 70 |
| Lecithin | 5 | 5 | 10 | — | 30 | — |
| Magnesium carbonate | 5 | — | — | — | — | — |
| Calcium carbonate | — | 5 | 2 | 10 | — | 30 |
| Dissolving rate (%) | | | | | | |
| Corresponding to the rumen | 17 | 15 | 21 | 5 | 71 | 82 |
| Corresponding to the abomasum | 20 | 26 | 38 | 15 | 27 | 10 |
| Corresponding to the small intestines | 60 | 59 | 37 | 16 | 1 | 3 |

TABLE 3

|  | EXAMPLE | | | | |
| --- | --- | --- | --- | --- | --- |
|  | 10 | 11 | 12 | 13 | 14 |
| Biologically active substance | Lysine-HCl | Methionine | Lysine-HCl | Lysine-HCl | Lysine-HCl |
| Cores (parts by weight) | 100 | 100 | 100 | 100 | 100 |
| Coated layer (parts by weight) | 33 | 33 | 25 | 33 | 33 |
| Composition of the coating layer (%) | | | | | |
| Beef tallow | 90 | 90 | 90 | 90 | 90 |
| Lecithin | 5 | 5 | 5 | 5 | 5 |
| $CaHPO_4 \cdot 2H_2O$ | 5 | | | | |
| $CaH_2P_2O_7$ | | 5 | | | |
| $Mg(OH)_2$ | | | 5 | | |
| $NaHCO_3$ | | | | 5 | |
| $Fe_2O_3$ | | | | | 5 |
| Thickness of the film (μm) | 60 | 15 | 50 | 30 | 40 |
| Dissolving rate (%) | | | | | |
| Corresponding to the rumen | 10 | 11 | 22 | 28 | 15 |
| Corresponding to the abomasum | 14 | 11 | 16 | 15 | 18 |
| Corresponding to the small intestines | 59 | 60 | 41 | 51 | 46 |

All publications disclosed herein are incorporated by reference. Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A feed additive for ruminants comprising a core containing a biologically active substance and a coating composition placed on the surface of said core, said coating composition comprising from 0.1 to 20% lecithin, 0.1 to 10% of at least one inorganic substance which is a member selected from the group consisting of calcium hydrogen phosphate hydrate; calcium dihydrogen pyrophosphate; magnesium pyrophosphate; magnesium hydrogen phosphate hydrate; aluminum phosphate; magnesium hydroxide; aluminum hydroxide; ferrous oxide; ferric oxide, manganese oxide; zinc oxide; and sodium hydrogen carbonate, and at least one substance selected from the group consisting of straight-chain or branched-chain saturated or unsaturated monocarboxylic acid having 14 to 22 carbon atoms, salts thereof, hardened vegetable oils, hardened animal oils, and waxes.

2. A feed additive for ruminants according to claim 1, wherein said inorganic substance is selected from the group consisting of calcium hydrogen phosphate dihydrate; calcium dihydrogen pyrophosphate; magnesium hydroxide; sodium hydrogen carbonate; and ferric oxide.

3. A feed additive for ruminants according to claim 1, wherein said inorganic substance is calcium hydrogen phosphate dihydrate.

4. A feed additive for ruminants according to claim 1, wherein said inorganic substance is calcium dihydrogen pyrophosphate.

5. A feed additive for ruminants according to claim 1, wherein said inorganic substance is magnesium hydroxide.

6. A feed additive for ruminants according to claim 1, wherein said inorganic substance is sodium hydrogen carbonate.

7. A feed additive for ruminants according to claim 1, wherein said inorganic substance is ferric oxide.

8. A feed for ruminants comprising a feed additive according to claim 1.

* * * * *